US00PP36353P3

(12) United States Plant Patent
Schoone

(10) Patent No.: US PP36,353 P3
(45) Date of Patent: Dec. 31, 2024

(54) ***PHALAENOPSIS* PLANT NAMED 'Time Bandit'**

(50) Latin Name: *Phalaenopsis hybrida*
Varietal Denomination: Time Bandit

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/527,365

(22) Filed: Dec. 3, 2023

(65) Prior Publication Data

US 2024/0188469 P1 Jun. 6, 2024

Related U.S. Application Data

(60) Provisional application No. 63/430,035, filed on Dec. 4, 2022.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02; A01H 5/00; A01H 6/62
See application file for complete search history.

(56) References Cited

U.S. PATENT DOCUMENTS

PP30,220 P3 * 2/2019 Schoone ..... A01H 6/62
Plt./311

OTHER PUBLICATIONS

Floricultura Time Bandit 334348, retrieved on Apr. 30, 2024 at https://www.floricultura.com/en/orchidaceae/floriclone-phalaenopsis/standard/334348/, 2 pp. (Year: 2024).*
CPVO Application Consultation Version 4.20.4 for *Phalaenopsis* Time Bandit retrieved on Aug. 13, 2024 at https://online.plantvarieties.eu/publicConsultationDetails?registerId=20221923&denomination=time%20bandit, 2 pp. (Year: 2024).*

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'Time Bandit', characterized by its upright plant habit; moderately vigorous to vigorous growth habit; strong flowering stems; strong leaves; freely flowering habit with typically two inflorescences developing per plant, each inflorescence with numerous flowers; flowers with reddish purple-colored petals, sepals and labella; and good postproduction longevity.

2 Drawing Sheets

Figure 1:
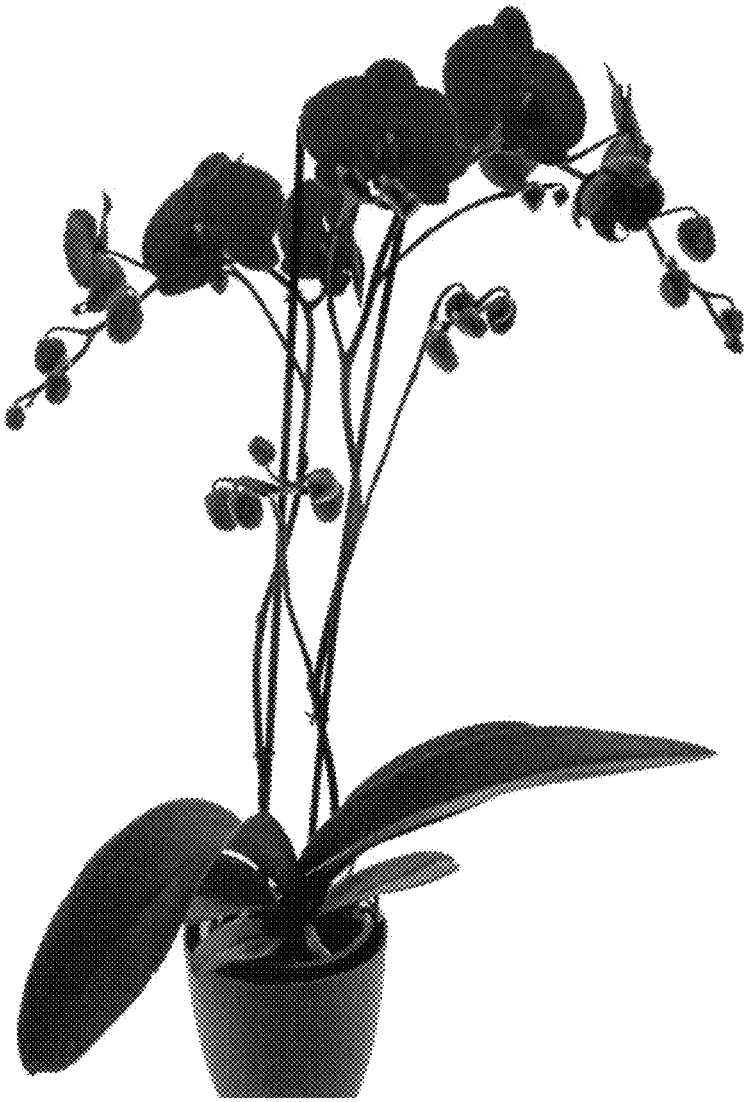

Botanical designation: *Phalaenopsis hybrida.*
Cultivar denomination: 'TIME BANDIT'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B. V. of Heemskerk, The Netherlands on Aug. 15, 2022, application number 2022/1923. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Time Bandit'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in April 2013 in Assendelft, The Netherlands of a proprietary selection of *Phalaenopsis hybrida* identified as code number 2303, not patented, as the female, or seed, parent with *Phalaenopsis hybrida* 'Joyride', disclosed in U.S. Plant Pat. No. 29,153, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in October, 2018.

Asexual reproduction of the new *Phalaenopsis* plant by in vitro meristem propagation in a controlled environment in Assendelft, The Netherlands since October, 2019 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Time Bandit'. These characteristics in combination distinguish 'Time Bandit' as a new and distinct *Phalaenopsis* plant:

1. Upright plant habit.
2. Moderately vigorous to vigorous growth habit.
3. Strong flowering stems.
4. Strong leaves.
5. Freely flowering habit with typically two inflorescences developing per plant, each inflorescence with numerous flowers.
6. Flowers with reddish purple-colored petals, sepals and labella.
7. Good postproduction longevity.

Plants of the new *Phalaenopsis* can be compared to plants of the female parent selection. Plants of the new *Phalaenopsis* differ primarily from plants of the female parent selection in the following characteristics:

1. Flower petals of plants of the new *Phalaenopsis* are not imbricate whereas flower petals of plants of the female parent selection are very close to imbricate.
2. Flower petals of plants of the new *Phalaenopsis* are reddish purple in color whereas flower petals of plants of the female parent selection are soft purplish red in color.

Plants of the new *Phalaenopsis* can be compared to plants of the male parent, 'Joyride'. Plants of the new *Phalaenopsis* differ primarily from plants of 'Joyride' in the following characteristics:

1. Flower petals of plants of the new *Phalaenopsis* are not imbricate whereas flower petals of plants of 'Joyride' are imbricate.
2. Flower petals of plants of the new *Phalaenopsis* are reddish purple in color whereas flower petals of plants of 'Joyride' are purple/violet in color.
3. Flower labella of plants of the new *Phalaenopsis* are reddish purple in color whereas flower labella of plants of 'Joyride' are purple in color.

Plants of the new *Phalaenopsis* can be compared to plants of *Phalaenopsis hybrida* 'Freeride', disclosed in U.S. Plant Pat. No. 30,220. In side-by-side comparisons, plants of the new *Phalaenopsis* differ primarily from plants of 'Freeride' in the following characteristics:

1. Flower petals of plants of the new *Phalaenopsis* are not imbricate whereas flower petals of plants of 'Freeride' are imbricate.
2. Flower petals of plants of the new *Phalaenopsis* are reddish purple in color whereas flower petals of plants of 'Freeride' are purple/violet in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Time Bandit' grown in a container.

Figure 2:
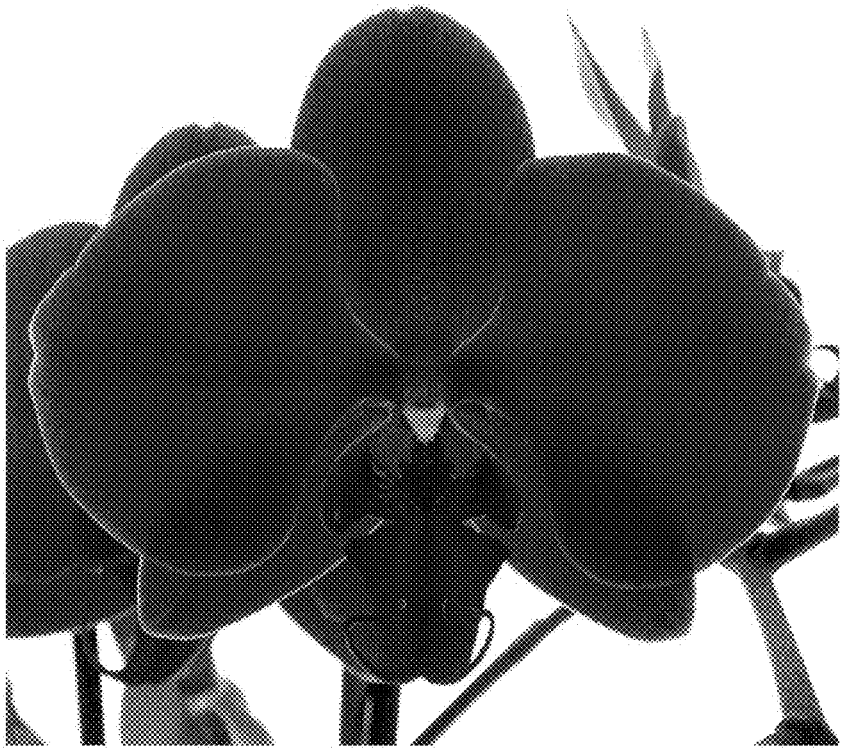

The photograph on the second sheet (FIG. 2) is a close-up view of a typical flower of 'Time Bandit'.

DETAILED BOTANICAL DESCRIPTION

The aforementioned photographs and following observations and measurements describe plants grown during the early spring in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Time Bandit'.

Parentage:

*Female, or seed, parent.*—Proprietary selection of *Phalaenopsis hybrida* identified as code number 2303, not patented.

*Male, or pollen, parent.*—*Phalaenopsis hybrida* 'Joyride', disclosed in U.S. Plant Pat. No. 29,153.

Propagation:

*Type.*—By in vitro meristem propagation.

*Time to initiate roots, summer and winter.*—About two weeks at temperatures about 28 C to 30 C.

*Time to produce a rooted young plant, summer and winter.*—About 20 to 25 weeks at temperatures about 28 C to 30 C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically four inflorescences developing per plant, each inflorescence with numerous flowers; monopodial; moderately vigorous to vigorous growth habit and moderate growth rate.

*Plant height, substrate level to top of foliar plane.*—About 13.2 cm.

*Plant height, substrate level to top of floral plane.*—About 50.8 cm.

*Plant diameter or spread.*—About 38.9 cm.

Leaf description:

*Arrangement and quantity.*—Distichous, simple; sessile; about three fully-developed leaves per plant.

*Length.*—About 27.3 cm.

*Width*.—About 7.8 cm.

*Aspect*.—Semi-erect to horizontal and eventually outwardly arching.

*Shape*.—Narrowly oblong; moderately carinate and moderately reflexed.

*Apex*.—Unequal acute.

*Base*.—Sheathing. Sheath length: About 1.8 cm. Sheath width: About 1.3 cm. Sheath color: Close to 146B strongly tinged with close to 187A and 187B.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to 146A. Developing leaves, lower surface: Close to 146B; towards the margins and along the midvein, strongly tinged with close to 187A. Fully expanded leaves, upper surface: Close to 137A; venation, close to 147A. Fully expanded leaves, lower surface: Close to 146B; towards the margins, tinged with close to a blend of N186B and N186C; venation, close to 143A.

Inflorescence description:

*Appearance and flowering habit*.—Showy zygomorphic flowers arranged on axillary simple or branched racemes; typically two inflorescences develop per plant; each inflorescence with about 17 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 41 cm.

*Inflorescence width*.—About 22 cm.

*Flower buds*.—Height: About 2.1 cm. Diameter: About 1.5 cm by 1.7 cm. Shape: Broadly ovate. Color: Close to a blend of N79B and 187C.

*Flower size*.—About 8.4 cm (vertical) by 9.6 cm (horizontal).

*Flower depth*.—About 2.9 cm.

*Petals, quantity and arrangement*.—Three, two lateral petals and one center petal transformed into a labellum.

*Lateral petals*.—Length: About 4.8 cm. Width: About 5.8 cm. Shape: Broadly reniform to close to lunate. Apex: Retuse. Margin: Entire; not undulate. Texture and luster, upper and lower surfaces: Smooth, glabrous, velvety; matte. Color: When opening, upper surface: Close to a blend of N78A and N79C; towards the base, close to N79C; midvein, close to N79C. When opening, lower surface: Close to N75A to N75C; towards the margins, close to 77A; venation, close to 77A. Fully opened, upper surface: Close to NN78A; at the base, close to a blend of N78A and NN78A; midvein, close to a blend of N78A and NN78A; Fully opened, lower surface: Close to a blend of N78C and N80B; towards the margins, close to N80B; venation, close to N78A to a blend of N78A and N78B; color does not change with subsequent development. color does not change with subsequent development.

*Labella*.—Appearance: Three-parted with two lateral lobes and a central lobe. Length, lateral lobes: About 2.3 cm. Width, lateral lobes: About 1.6 cm. Length, central lobe: About 2.4 cm. Width, central lobe: About 1.2 cm to 2.3 cm. Length, cirrhose tips: About 1.6 cm. Shape, lateral lobes: Obovate. Shape, central lobe: Deltoid. Apex, lateral lobes: Obtuse. Apex, central lobe: Cleft with two reflexed cirrhose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 6 mm in width and about 6.5 mm in height. Color: When opening and fully opened, upper surface: Lateral lobes: Close to N78A; towards the base, close to N79D with stripes, close to 155A. Central lobe: Close to a blend of N78A and N79C; at the base, N78D with stripes, close to N79C; midvein, close to N79C; cirrhose tips, close to N79C. Callosities: Close to 22A to 22B with fine dots, close to 183A. When opening and fully opened, lower surface: Lateral lobes: Close to N78A; proximally, close to N155A. Central lobe: Close to N78B; center, close to N78C; towards the apical margins, close to N78A; at the base, close to 182D; cirrhose tips, close to N78A.

*Sepals*.—Quantity and arrangement: Three, one upper dorsal sepal and two lower lateral sepals. Length, dorsal sepal: About 4.5 cm. Width, dorsal sepal: About 3.4 cm. Length, lateral sepals: About 4.7 cm. Width, lateral sepals: About 3 cm. Shape, dorsal sepal: Broadly elliptic. Shape, lateral sepals: Ovate to broadly elliptic. Apex, dorsal sepal: Retuse. Apex, lateral sepals: Broadly acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to N79C with fine dots, close to 77D; venation, close to N79B. When opening, lower surface: Close to N77B; towards the margins and apex, close to N78A; venation, close to N79B. Fully opened, upper surface: Close to a blend of N78A and NN78A with fine dots, close to 77D; venation, close to N79C; color does not change with subsequent development. Fully opened, lower surface: Close to N80B; center, closer to N78A; venation, close to N79C; color does not change with subsequent development. Color, lateral sepals: When opening, upper surface: Close to a blend of N78A and N79C with fine dots, close to 77D; at the base, tinged with close to 155C; venation, close to N79B. When opening, lower surface: Close to N77B; venation, close to N79B. Fully opened, upper surface: Close to N78A with fine dots, close to 77D; at the base, tinged with close to 155C; venation, close to N79C; color does not change with subsequent development. Fully opened, lower surface: Close to N78B; venation, close to N78A; color does not change with subsequent development.

*Peduncles*.—Length: About 61 cm. Diameter: About 5.5 mm. Strength: Strong. Aspect: Upright to outwardly arching. Texture and luster: Smooth, glabrous; matte. Color: Close to N200A with dots and marbling, close to 148D.

*Pedicels*.—Length: About 4.7 cm. Diameter: About 3.5 mm. Strength: Moderately strong. Aspect: About 50 degrees from peduncle axis. Texture and luster: Smooth, glabrous; matte. Color: Close to 199C; proximally, close to N186C and distally, close to 77D.

*Reproductive organs*.—Androecium: Column length: About 9 mm. Column width: About 6 mm. Column color: Close to N78A. Pollinia quantity: Two. Pollinia diameter (per two pollinia): About 3 mm. Pollinia color: Close to 23A. Gynoecium: Stigma length: About 4 mm. Stigma width: About 5 mm. Stigma shape: Reniform. Stigma color: Close to N155A. Ovary length: About 1 cm. Ovary diameter: About 1 mm. Ovary color: Close to 150C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Time Bandit' as herein illustrated and described.

* * * * *